(12) United States Patent
Falcone

(10) Patent No.: US 6,187,954 B1
(45) Date of Patent: Feb. 13, 2001

(54) SYNTHESIS OF FLUORINATED AMIDES

(75) Inventor: Samuel J. Falcone, San Jose, CA (US)

(73) Assignee: Seagate Technology LLC, Scotts Valley, CA (US)

( * ) Notice: Under 35 U.S.C. 154(b), the term of this patent shall be extended for 0 days.

(21) Appl. No.: 09/533,210

(22) Filed: Mar. 23, 2000

Related U.S. Application Data

(60) Provisional application No. 60/144,268, filed on Jul. 15, 1999.

(51) Int. Cl.$^7$ .................................................. C07C 231/00
(52) U.S. Cl. ............................................... 564/136
(58) Field of Search .............................. 564/136

(56) References Cited

U.S. PATENT DOCUMENTS

| | | |
|---|---|---|
| 2,502,478 | 4/1950 | Padbury et al. . |
| 2,523,470 | 9/1950 | Kropa et al. . |
| 2,862,024 | 11/1958 | Rendall et al. . |
| 3,544,618 | 12/1970 | Dorfman et al. . |
| 3,719,698 | 3/1973 | Tesoro et al. . |
| 4,735,848 | 4/1988 | Kondo et al. . |
| 4,845,268 | 7/1989 | Ohsaka et al. . |
| 4,897,211 | 1/1990 | Dekura et al. . |
| 5,000,864 | 3/1991 | Stepparola et al. . |
| 5,188,747 | 2/1993 | Kai et al. . |
| 5,391,811 | 2/1995 | Bohm et al. . |
| 5,476,974 | 12/1995 | Moore et al. . |
| 5,506,309 | 4/1996 | Bierschenk et al. . |
| 5,606,098 | * 2/1997 | Ryabinin et al. . |
| 5,637,748 | 6/1997 | Hung et al. . |
| 5,717,037 | 2/1998 | Saito et al. . |
| 5,900,318 | 5/1999 | Yanagisawa . |
| 5,962,117 | 10/1999 | Furutani et al. . |

* cited by examiner

Primary Examiner—Gary Geist
Assistant Examiner—Devesh Khare
(74) Attorney, Agent, or Firm—McDermott, Will & Emery

(57) ABSTRACT

A fluoropolyalkylether is prepared under mild reaction conditions by combining a fluoropolyalkylether substituted with one or more ester end-groups with an amine. Embodiments include combining: (i) a fluoropolyalkylether substituted with one or more ester end-groups having the formula:

$$Rf—(COOR')_q$$

with (ii) an amine having the formula:

$$HNR_1R_2$$

and (iii) a solvent comprising a hydrofluorocarbon or a hydrofluoroether together with a lower alcohol at a temperature of from about 15° C. to about 30° C. to form the fluoropolyalkylether amide, where Rf is a perfluoropolyether, R' is a lower alkyl group, q is 1–4; $R_1$ is H and $R_2$ is a $C_2$–$C_4$ or a $C_2$–$C_4$ substituted with at least one hydroxyl group.

14 Claims, No Drawings

SYNTHESIS OF FLUORINATED AMIDES

CROSS-REFERENCE TO RELATED APPLICATION

This application claims priority from provisional patent application Ser. No. 60/144,268 filed Jul. 15, 1999 entitled "SYNTHESIS OF FLUORINATED AMIDES" the entire disclosure of which is herein incorporated by reference.

FIELD OF THE INVENTION

The present invention relates to the preparation of fluorinated polyether amides, particularly the synthesis of perfluoropolyalkylethers having amide terminal groups. The invention has particular applicability to the preparation of fluorinated polyether amides which are useful as lubricants for magnetic recording medium.

BACKGROUND OF THE INVENTION

Fluoropolyether lubricants are of particular interest in lubricating magnetic recording media. These lubricants are uniquely suited to form lubricant topcoats on magnetic media because of such properties as chemical inertness, low vapor pressure, low surface tension, high thermal stability, stability under high shear stress and good boundary lubrication properties. Among the many lubricants available, liquid perfluoropolyethers (PFPE) are the most typically used in forming topcoat lubricants on magnetic recording media.

Commercially available PFPE lubricants include Krytox from DuPont, Demnum from Daikin Industries and Fomblin Z and Y fluids from Montedison. Many of the commercial PEPE lubricants are substituted with 14 polar end-groups, such as one or more hydroxyl, or carboxylic acid groups. The polar end-groups are considered necessary to improve adhesion of the lubricants to the surface of a magnetic recording medium. Several fluorinated polyakylether amides have recently proven useful in forming lubricant topcoats on magnetic recording media These lubricants can be conventionally prepared by combining an acid chloride with an amine. For example, U.S. Pat. No. 4,897,211 discloses the preparation of a synthetic magnetic recording lubricant by reacting a perfluoropolyalkylether acid chloride with an amine at elevated temperatures to produce the amide. This method, however, requires the use of air and moisture sensitive acid chlorides. Further, acid chlorides of fluoropolyether lubricants are not readily available, thus necessitating an additional step for their preparation prior to their reaction with the amine compound to form the amide.

Lower weight fluorinated compounds have also been used for the synthesis of lower weight fluorinated alkyl amides. See, e.g., U.S. Pat. Nos. 2,502,478 and 2,523,470 which are directed to the preparation of amide derivatives of tetrafluorosuccinic acid. These preparations, however, are not related to the synthesis of polymeric fluoroyalkylether amides and the products discloses therein are not useful as lubricants for magnetic recording media. Further, it is believed that the preparations used in synthesizing low weight amides are not amenable to preparing polymeric fluoropolyalkylether lubricants.

Other preparations of amides includes reacting fluorinated compounds with ammonia as in U.S. Pat. Nos. 2,862,024 and 3,544,618. These references disclose reaction conditions that require low temperatures to produce the amides. Further the disclosed compounds are not related to magnetic recording media lubricants such as fluoropolyalkylether amides.

The preparation of fluorinated amides as intermediates in the formation of nitrites have further been disclosed, as in U.S. Pat. Nos. 5,637,748 and 5,717,037. As discussed in the 5,637,748 patent to Hung, the solubility of fluorinated compounds are typically low, thus requiring special procedures and/or handling to achieve high yield products. It is believed that these difficulties are exacerbated when preparing high molecular weight compounds, such as polymeric fluoroalkylethers. Additionally, these references, as others in the art disclose that the preparation of the amides from ammonia require low temperatures.

Accordingly a continuing need exists in the magnetic lubrication art to produce fluoropolyalkylether derivatives in direct and economical means from commercially available products. In particular a need has been demonstrated to synthesize fluorinated amides useful in magnetic recording lubrication without the use of air sensitive intermediates and/or harsh reaction conditions.

SUMMARY OF THE INVENTION

An aspect of the present invention is a facile method of preparing a synthetic fluoropolyalkylether amide lubricant for a magnetic recording medium.

Additional aspects and other features of the invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other aspects are achieved in part by a method of preparing a synthetic fluoropolyalkylether amide lubricant for a magnetic recording medium. The method comprises combing (i) a fluoropolyalkylether substituted with one or more ester end-groups and (ii) a primary or secondary amine. The reaction can advantageously be carried out under mild conditions, e.g., at a temperature of from about 15° C. to about 30° C. The method of the present invention further eliminates the use of acid chlorides, anhydrides and/or other air sensitive intermediates and elevated or low temperatures. In accordance with the present invention, the method of preparing a synthetic fluoropolyalkylether amide lubricant is advantageously carried out without the aid of a catalyst to form the fluoropolyalkylether amide.

Embodiments of the present invention include combining the fluoropolyalkylether substituted with one or more ester end-groups with the primary or secondary amine at a temperature of from about 20° C. to about 25° C. to form the fluoropolyalkylether amide.

In an embodiment of the present invention the product is a fluoropolyalkylether amide having the formula:

$$Rf-(CONR_1R_2)_q$$

wherein Rf is a fluoropolyalkylether; $R_1$ and $R_2$ are independently substituted or unsubstituted alkyl or alkenyl groups; and q is 1–4.

The fluoropolyalkylether substituted with one or more ester end-groups has the formula:

$$Rf-(COOR')_q$$

wherein Rf is a fluoropolyalkylether; R' is a lower alkyl group and q is 1–4. The fluoropolyalkylether ester can be readily prepared by combining commercially available fluoropolyether carboxylic acids with an ortho ester, such as trimethyl or triethyl orthoformate.

Embodiments include fractionating the fluoropolyalkylether substituted with one or more ester end-groups to a polydispersity index of less than about 1.5 prior to combining the ester with the amine. In an embodiment of the present invention the fluoropolyalkylether ester has a number average molecular weight of about 4,000–20,000 a.m.u.

Additional advantages of the present invention will become readily apparent to those having ordinary skill in the art from the following detailed description, wherein the embodiments of the invention are described, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE INVENTION

The present invention stems from the surprising discovery that certain fluoropolyether amide compounds can be prepared from their respective esters under mild reaction conditions, i.e., the reaction can be carried out at room temperature. A particularly advantageous aspect of the present invention is the ability to produce the fluoropolyether amides without the use of catalysts or additional acids or bases.

In practicing the invention, a synthetic fluoropolyalkylether amide lubricant for a magnetic recording medium, is prepared by combining a fluoropolyalkylether substituted with one or more ester end-groups with a primary or secondary amine. The reaction is carried out at about room temperature to form the fluoropolyalkylether amide, without the use of a catalyst. As used herein, a catalyst is a substance that accelerates the reaction between the fluoropolyalkylether ester with the amine but is not consumed or permanently changed. Hence, the present invention provides a facile method of preparing a synthetic fluoropolyalkylether amide lubricant by simply admixing the reagents at about room temperature.

In an embodiment of the present invention, the product is a fluoropolyalkylether amide having the formula:

$$Rf\text{—}(CONR_1R_2)_q$$

wherein Rf is a fluoropolyalkylether; $R_1$ and $R_2$ are independently substituted or unsubstituted alkyl or alkenyl groups; and q is 1–4.

Fluoropolyalkylether amides of the present invention include homopolymers, random polymers or block polymers, i.e. the repeating units of the fluoropolyether, Rf, may be the same or different. In addition, different repeat units of Rf can be randomly distributed along the backbone of the polymer or distributed as a block of one type of repeat unit and subsequent blocks of different repeat units along the backbone of the polymer. The inventive lubricants can be completely fluorinated or partially fluorinated and can be linear or branched. In an embodiment of the present invention, Rf is a perfluoropolyether comprising a plurality of $-(C_aF_{2a}O)_n-$ repeating units, wherein subscript a is independently in each such unit an integer of from 1 to about 10 and n is an integer from 2 to about 200. In an embodiment of the present invention n is an integer from about 10 to about 100, e.g. from about 20 to about 80.

Representative perfluoropolyalkylethers of the foregoing have the following formulas:

$$-(CF_2CF_2O)_n-(CF_2O)_m-$$
$$-(CF(CF_3)CF_2O)_n-(CF_2O)_m-$$
$$(CF_2CF_2CF_2O)_n-$$
$$-(CF(CF_3)CF_2O)_n-$$

wherein n and m, combined, are from about 10 to 100. In an embodiment of the present invention, the fluoropolyether amides have a number average molecular weight of about 1,000 to about 20,000 a.m.u., e.g., about 2,000 to about 5,000 a.m.u.

In carrying out the inventive process, it is advantageous to fractionate the fluoropolyalkylether ester prior to combining the ester with the amide. Such fractionation steps comprise distillation or chromatography. Fluoropolyethers esters with a narrow molecular weight distribution yield a narrow molecular weight product amide. The molecular weight distribution can be measured by a variety of conventional techniques including Gel Permeation Chromatography (GPC). The molecular weight distribution of a polymer is determined by the ratio of the weight average (Mw) to number average (Mn) molecular weight of a given polymer. The Mw/Mn value of a given polymer is referred to as its polydispersity index. The fluoropolyether has a polydispersity index of less than about 1.5, e.g, less than about 1.2.

In an embodiment of the present invention, the polyalkylether amide is prepared by combining: a perfluoropolyalkylether substituted with one or more ester end-groups having the formula:

$$Rf\text{—}(COOR')_q$$

with an amine having the formula:

$$HNR_1R_2$$

wherein Rf comprises a plurality of $-(C_aF_{2a}O)_n-$ repeating units, wherein subscript a is independently in each such unit an integer of from 1 to about 10 and n is an integer from 10 to about 60; R' is a lower alkyl group, such as a methyl, ethyl, propyl, butyl, pentyl, or a structural isomer thereof and q is 1–4.

In the amine of the above embodiment, $R_1$ represent H and $R_2$ is a $C_2$–$C_4$ group or a $C_2$–$C_4$ alkyl group substituted with at least one hydroxyl group. Representative amines useful in the preparation of the inventive fluoropolyalkylether amides include the following:

NH$_2$CH$_2$CH(OH)CH$_2$OH
NH$_2$CH$_2$CH$_2$OCH$_2$CH$_2$OH
NH(CH$_2$CH$_2$OH)$_2$
NHCH$_2$CH$_2$CH$_2$Si(OCH$_3$)$_3$
NH$_2$CH$_2$(Y)$_x$CH$_2$NH$_2$
NH$_2$CH$_2$(CH$_2$CH$_2$O)$_x$CH$_2$NH$_2$
NH$_2$CH$_2$(Y)$_x$CH$_3$ wherein x is an integer of from 1–15 and Y is a saturated or unsaturated alkyl, or aryl group substituted with one or more halogen, hydroxyl, crotyl, cinnamyl, sulfur, or silyl group.

In practicing the invention, the reaction can be carried out in a solvent comprising a hydrofluorocarbon or a hydrofluoroether together with a lower alcohol, such as methanol, ethanol, propanol, butanol etc., or structural isomers thereof. In accordance with the present invention, the reaction is carried out at room temperature, i.e. at a temperature of from about 15° C. to about 30° C. to form the fluoropolyalkylether amide.

Hydrofluorocarbon or hydrofluorether solvent useful in the present invention include conventional solvents, such as PF-5060 (i.e. $C_7F_{16}$) (3M Corp.), HFE-7100 (i.e.

$C_4F_9OCH_3$) (3M Corp.), HFE-7200 (i.e. $C_4F_9OC_2H_5$) (3M Corp.), Freon TA, Vertrel-XF (i.e. $C_5H_2F_{10}$) (Dupont) or AK-225 (i.e. ($C_3HCl_2F_5$) (AGA Chemical Asahiklin). Product work up and purification is easily accomplished by distilling the solvents from the reaction mixture by rotary evaporation and removing any excess amine component by vacuum distillation. After distillation, the product amides prepared by the present invention can be recovered in greater than about 90% purity. Thus, no further purification step, such as a chromatography step, is generally required prior to employing the product amides as high performance thin film lubricants.

In practicing the present invention, the fluoropolyalkylethers having amide terminal groups are particularly applicable for lubricating magnetic recording media The amide lubricants of the present invention can be prepared having a number average molecular weight of greater than about 1,000 a.m.u., e.g., greater than about 4,000 a.m.u. High molecular weight amide lubricants, e.g., greater than about 8,000 a.m.u., can also be prepared by the present invention. The amide lubricant of the present invention can be applied to a magnetic recording medium, either on the magnetic layer or on a conventionally applied protective overcoat, particularly a carbon overcoat. In an embodiment of the present invention, the lubricant is dissolved in a conventional hydrofluorocarbon or hydrofluorether solvent, such as PF-5060 in a ratio of about 0.0001% to about 100% by (weight/weight), preferably about 0.0005% to about 0.5%, more preferably about 0.001% to about 0.01%.

A typical magnetic recording medium, for example, a composite comprising a non-magnetic substrate having sequentially deposited on each side thereof an underlayer, a magnetic layer, and a protective carbon overcoat, is submerged in the lubricant solution and then slowly withdrawn therefrom. In practicing the present invention, one can employ a conventional lifter-type dipper to submerge the composite in the lubricant solution. One having ordinary skill in the art can easily optimize the duration of submergence and the speed of withdrawal to achieve a desired coating thickness.

EXAMPLES

1. Reaction of Z-deal methyl ester with aminopropanediol

A 250 ml round bottom flask was charged with 4.6 g (50.5 mmol) of 3-amino-1,2-propane diol and dissolved in 20 ml of a one to one mixture of methanol and BFE 7200. To this well stirred solution, under nitrogen, was dropwise added a solution of Z-deal (55 g, 25 mmol) in about 50 ml of HFE 7200. Z-deal is a perfluoropolyalkylether having the following formula:

and was obtained from Ausimont (Thoroughfare, N.J.) having a number average molecular weight of about 4500.

The addition was completed within about 20 minutes and thereafter the solution was stirred at room temperature overnight. An additional 0.3 ml of the amine was added to the reaction mixture and stirring continued for an additional 12 hours. After this time, the solvent was removed by rotary evaporation (at about 70° C. under 200 Torr) to yield 58.2 grams of a clear oil (about a 100% yield). The oil was purified by distillation at about 170° C. under about 0.5 Torr to yield about 55.5 g of a clear oil of the product amide to give a purified yield of about 95%.

2. Preparation of perfluoropolyether methyl ester and reaction of the perfluoropolyether methyl ester with aminopropanediol

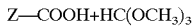

A 50 ml round bottom flask under a blanket of nitrogen and having a magnetic stirrer was charged with 8.2 g (2.3 mmol) of Krytox 157 FSM and 1.7 ml (15.6 mmol) of trimethylorthoformate. Krytox is a perfluoropolyalkylether having the following formula:

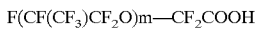

and was obtained from DuPont (Newark, Del.) having a number average molecular weight of about 4000.

After about two minutes, the reaction mixture was heated to reflux for about two hours to complete the conversion of the Krytox carboxylic acid to its ester. The trimethylorthoformate was then removed in vacuum at about 80–90° C. under a pressure of 10 Torr to provide the pure perfluoropolyether ester.

The prepared ester was then dissolved in vertrel XF and a solution of 3-amino-1,2-propane diol (0.5 g) in 3 ml of methanol was added. The solution was refluxed (at a temperature of about 55° C.) for approximately 48 hours and then poured into about 200 ml of freon TF and extracted with dilute acid. The product was recovered in 95% yield as a viscous oil.

It is believed that by adding an excess of amine, e.g., about 10 to about 20 equivalence, the reaction temperature can be lowered such that the product amide can be prepared at room temperature.

3. Preparation of a high molecular weight perfluoroalkyl polyether amide

A high molecular weight Krytox, having a number average molecular weight of about 12,000 a.m.u., was obtained by fractionating commercially available Krytox from DuPont (Newark, Del.). The carboxylic acid end-group of the fractionated Krytox was converted to its ester by the process described in Example 3. Krytox having an amide end-group and having a number average molecular weight of about 12,000 was then prepared by combining the Krytox ester with aminopropane diol.

4. Reaction of Z-deal methyl ester with piperonylamine

About 4.05 g (2.03 mmol) of a fractionated Z-deal obtained from Ausimont (Thoroughfare, N.J.) and having a number average molecular weight of about 4500 was dissolved in about 5 ml of vertrel XF and 0.75 g (2.48 mmol) of piperonylamine was added thereafter. The mixture was stirred for about one hour at room temperature and then purified using silica to provide about 4.0 g of the product amide (about a 88% purified yield).

5. Reaction of Z-deal methyl ester with geranylamine

In to a glass vial was placed about 4.5 g (2.25 mmol) of fractionated Z-deal (Ausimont, Thoroughfare, N.J.) having a number average molecular weight of about 4500 was dissolved in about 5 ml of vertrel XF and 0.71 g (4.6 mmol) of geranylamine was added thereafter. The mixture was permitted to react at room temperature then poured over about 25 ml of 1 N HCl. The product was extracted with Vertrel XF and dried to yield 4.1 g of the product amide.

The present invention is not limited to any particular type of fluorpolyakylether ester or amine reagent, but can be employed using any of the specified reagents to form the produce fluorpolyakylether amide under mild reaction conditions. Only the preferred embodiment of the present inven-

What is claimed is:

1. A method of preparing a synthetic fluoropolyalkylether amide lubricant for a magnetic recording medium, which method comprises:

combining (i) a fluoropolyalkylether substituted with one or more ester end-groups with (ii) a primary or secondary amine, under mild conditions to form the fluoropolyalkylether amide, wherein the reaction is carried out without a catalyst.

2. The method of claim 1, comprising combining the fluoropolyalkylether substituted with one or more ester end-groups with the amine at a temperature of from about 15° C. to about 30° C.

3. The method according to claim 1, wherein the product is a fluoropolyalkylether amide having the formula:

$$Rf\text{—}(CONR_1R_2)_q$$

wherein Rf is a fluoropolyalkylether;

$R_1$ and $R_2$ are independently substituted or unsubstituted alkyl or alkenyl groups; and q is 1–4.

4. The method according to claim 1, wherein the fluoropolyalkylether substituted with one or more ester end-groups has the formula:

$$Rf\text{—}(COOR')_q$$

wherein Rf is a fluoropolyalkylether; R' is a lower alkyl group and q is 1–4.

5. The method according to claim 4, wherein Rf comprises a plurality of —$(C_aF_{2a}O)_n$— repeating units, wherein subscript a is independently in each such unit an integer of from 1 to about 10 and n is an integer from 5 to about 80.

6. The method according to claim 4, wherein R' is a methyl, ethyl propyl, butyl, pentyl or structural isomer thereof.

7. The method according to claim 1, wherein the fluoropolyalkylether substituted with one or more ester end-groups has a number average molecular weight of about 4,000 to about 20,000 a.m.u.

8. The method according to claim 1 further comprising the step of fractionating the fluoropolyalkylether substituted with one or more ester end-groups to a polydispersity index of less than about 1.5 prior to combining the ester with the amine.

9. The method according to claim 1, comprising combining the fluoropolyalkylether substituted with one or more ester end-groups with the primary or secondary amine at a temperature of from about 20° C. to about 25° C. to form the fluoropolyalkylether amide.

10. The method according to claim 1, comprising combining (i) the fluoropolyalkylether substituted with one or more ester end-groups having the formula:

$$Rf\text{—}(COOR')_q$$

wherein Rf comprises a plurality of —$(C_aF_{2a}O)_n$— repeating units, wherein subscript a is independently in each such unit an integer of from 1 to about 10 and n is an integer from 10 to about 60; R' is a lower alkyl group and q is 1–4;

(ii) the amine having the formula:

$$HNR_1R_2$$

wherein $R_1$ is H and $R_2$ is a $C_2$–$C_4$ group or a $C_2$–$C_4$ group substituted with at least one hydroxyl group; and (iii) a solvent comprising a hydrofluorocarbon or a hydrofluoroether together with a lower alcohol; at a temperature of from about 15° C. to about 30° C. to form the fluoropolyalkylether amide.

11. The method of claim 10, comprising preparing the fluoropolyalkylether substituted with one or more ester end-groups by combining a fluoropolyalkylether substituted with one or more carboxylic acid groups with an ortho ester.

12. The method of claim 10, wherein the fluoropolyalkylether substituted with one or more ester end-groups has a number average molecular weight of greater than about 4,000 a.m.u.

13. The method of claim 10, wherein the fluoropolyalkylether substituted with one or more ester end-groups has a number average molecular weight of greater than about 8,000 a.m.u.

14. The method according to claim 10, wherein q is 2.

* * * * *